United States Patent [19]

Hurado et al.

[11] Patent Number: Plant 6,923

[45] Date of Patent: Jul. 18, 1989

[54] APRICOT TREE, "JUDY'S DELIGHT"

[76] Inventors: Jasper Hurado; Doris A. Hurado, both of 4715 So. Cherry, Fresno, Calif. 93706

[21] Appl. No.: 225,490

[22] Filed: Jul. 28, 1988

[51] Int. Cl.[4] ..... A01H 5/00

[52] U.S. Cl. ..... Plt./39

[58] Field of Search ..... Plt. 39

*Primary Examiner*—Robert E. Bagwill

*Attorney, Agent, or Firm*—Worrel & Worrel

[57] ABSTRACT

A new and distinct variety of apricot tree which is denominated varietally as "Judy's Delight" and which is somewhat similar to the Katy Apricot Tree (U.S. Plant Pat. No. 4,339), with which it is most closely related, the subject variety characterized as to novelty by producing large fruit which have a light orange skin color and an orange flesh color and which are mature for commercial harvesting and shipment approximately May 15 through May 30 in the San Joaquin Valley of Central California.

1 Drawing Sheet

BACKGROUND OF THE NEW VARIETY

The present invention relates to an apricot tree which has been denominated varietally as "Judy's Delight" and more particularly to an apricot tree which produces fruit having an attractive light orange skin color and which ripen for harvesting approximately the same time of the season as the fruit produced by the Katy Apricot Tree (U.S. Plant Pat. No. 4,339) with which it is most closely similar, but from which it is distinguished therefrom and characterized principally as to novelty by producing fruit which are substantially larger in size than that produced by the Katy Apricot Tree and which further exhibits a characteristic skin color which is a lighter shade of orange than that typically displayed by the variety "Katy". In addition, the new variety of Apricot Tree hereof displays noteworthy storage characteristics and has a balanced and pleasant flavor which is uncommon to the variety to which it is most closely similar.

The Katy Apricot Tree (U.S. Plant Pat. No. 4,339) is well known as a producer of early maturing apricots, the fruit of the Katy Apricot Tree characterized by an orange skin color and having a date of maturity for harvesting and shipment during the second and third week of May in the San Joaquin Valley of Central California.

It has long been recognized that it would be desirable to have an apricot tree that somewhat remotely resembles the Katy Apricot Tree (U.S. Plant Pat. No. 4,339) and which further is ripe for commercial harvesting and shipment at approximately the same time of the season but which produces fruit which are substantially larger in size than the fruit produced by the "Katy" Apricot Tree and which further has an attractive light orange skin color and a balanced and pleasant flavor.

ORIGIN AND ASEXUAL REPRODUCTION OF THE NEW VARIETY

The new and distinct variety of apricot tree hereof was discovered in 1981 by the inventors as a chance seedling of unknown parentage growing in the cultivated area of the applicants' property which is located at 4715 South Cherry, in Fresno, Fresno County, Calif. The chance seedling was noted at that time to have desirable characteristics. The inventors observed the chance seedling for several years and scion wood of the new variety was subsequently taken by the applicants in 1985 and grafted into a test seedling which is located on the same property. It has been subsequently determined that this first asexual propagation resulted in progeny being produced that possessed the same distinctive characteristics as the original chance seedling.

SUMMARY OF THE NEW VARIETY

The Judy's Delight variety of Apricot Tree described herein is characterized principally as to novelty by producing fruit which are mature for commercial harvesting and shipment on or about May 15 through May 30, approximately at the same time in the season as the Katy Apricot Tree (U.S. Plant Pat. No. 4,339) with which it is most closely similar, but from which it is distinguished therefrom by producing an apricot which has a distinctive light orange skin coloration and which further has a larger size and a pleasant and well balanced flavor.

BRIEF DESCRIPTION OF THE DRAWINGS

The accompanying drawing is a color photograph of four mature fruit of the subject variety, one of which has been divided in the suture plane to show the flesh and stone characteristics, together with a twig bearing typical leaves showing the characteristic coloration thereof, all of the subject variety.

DETAILED DESCRIPTION

Referring more specifically to the pomological details of this new and distinct variety of apricot tree, the following has been observed under the ecological conditions prevailing at the property of the inventors which is located at 4715 So. Cherry, in Fresno, Fresno County, Calif. All major color code designations are by reference to the Dictionary of Color, by Maerz and Paul, Second Edition, 1950. Common color names are also employed occasionally.

TREE

Size:

*Generally.*—Medium to large depending upon pruning practices.

Vigor: Vigorous and hardy when grown under typical San Joaquin Valley climatic conditions.

Figure: Upright and occasionally upright spreading; the eventual form of the tree may be modified somewhat by pruning practices.

Productivity: Dense and productive, regular.

Trunk:

*Size.*—Generally — large.

*Texture of bark.*—Moderately rough and having a moderate number of fissures.

*Bark color.*—Greyish-brown (8-A-9).

Branches:

*Diameter.*—Average.

*Texture of bark.*—Average in texture.

*Color.*—One year old wood — brown (7-E-10).

*Lenticels.*—One year old wood — numerous light-brown lenticels are evident, (13-D-8).

*Color.*—Current season growth — light green, (20-I-6).

Further, the current season growth may often be tinged with red in the vicinity of exposed surfaces. Moreover, the growing tips of immature young shoots may also have a reddish-orange color.

*Surface texture.*—Current season growth — smooth.

LEAVES

Size:

*Generally.*—Large.

*Average length, including the petiole.*—Approximately 14.6 cm.

*Average Width.*—Approximately 9.4 cm.

*Form.*—Generally — ovate and occasionally ovate-cordate.

Color:

*Upper leaf surface.*'Dark green, (24-J-8).

*Lower leaf surface.*—Light green, (23-E-6).

*Mid-vein.*—Pale green, (20-J-4).

*Mid-vein.—Size.*—The upper leaf mid-vein is prominent and is approximately one millimeter in diameter.

Leaf margins:

*Form.*—Variable. The leaf margins of large vigorous leaves appear uniformly serrate. Smaller leaves and those leaves found growing on small spurs often appear finely crenate.

Petiole:

*Length.*—Moderately long, approximately 30 mm.

*Thickness.*—Approximately 2 mm.

*Color.*—Light green (20-F-5).

Leaf glands:

*Numbers.*—Variable, one through five may be evident. As a general matter only two glands were found on the leaf margin and one to five leaf glands appear on the leaf petiole.

*Size.*—Small and globose.

*Position.*—Generally — The leaf glands are located on both the leaf petiole, and the basal leaf margin.

*Color.*—Shiny green, (20-I-4). The leaf glands often have a red color when they are immature, however, they darken and deteriorate with advancing age.

Petiole glands:

*Position.*—The glands positioned on the leaf petiole are usually located in the vicinity of mid-petiole and in pairs. These particular glands appear slightly alternate in position.

Stipules:

*Generally.*—Two stipules often appear and subtend the petiole base.

*Length.*—Approximately 5 mm.

*Width.*—Variable, approximately 2 to 3 mm.

*Shape.*—Broad and having long sharp serrations.

*Color.*—Light green, approximately (19-H-4). The stipules are often tinged with red.

*Petiole stipules.*—These stipules are considered to be early deciduous.

*Leaf margin stipules — generally.*—Two stipules occur at this location. These particular stipules are considered persistent and are generally irregular in form, and most often appear roughly oval in shape.

*Leaf margin stipules — color.*—These particular stipules have approximately the same coloration as the leaf; upper surface — a dark green, (24-J-8); lower surface — a lighter grey-green (23-E-6).

*Leaf margin stipule — length.*—Approximately 5 to 6 mm.

Flowers: The lower buds and flowers of the subject variety are not particularly distinctive.

FRUIT

Maturity when described: Ripe for commercial harvesting and shipment approximately May 15 through May 30 under the ecological conditions prevailing in the San Joaquin Valley of Central California.

Size:

*Uniformity.*—Uniform. The size of the instant variety is considered large for the species.

*Average cheek diameter.*—Approximately 60 mm.

*Average suture diameter.*—Approximately 64 mm.

*Average axial diameter.*—Approximately 61 mm.

Form:

*Uniformity.*—Uniform.

*Shape.*—Ovate in its lateral aspect and broadly oval in its basal aspect. As a general matter, the fruit appears narrower in the area between the cheeks as compared with the area between the ventral portion and the dorsal suture.

Suture:

*Generally.*—The suture appears as a distinct line which extends from the base to the apex and may be slightly to substantially depressed. A small amount of cross-stitching on the suture line may be evident particularly in those areas over or considered in the immediate vicinity of the apical shoulder.

*Color.*—The suture color blends in with the surrounding skin coloration.

*Form.*—The suture is deep and appears somewhat folded inside the stem cvity.

Ventral surface: Rounded and displaying a slight to moderate amount of lipping. Further, the sides appear somehwat slightly unequal with one side nearly always appearing larger than the other side.

Stem cavity:

*Generally.*—Moderately broad and oval in form.

*Depth.*—Approximately 8–10 mm.

*Width.*—Approximately 21–24 mm.

*Length.*—Approximately 26–28 mm.

Base:

*Form.*—Rounded and strongly oblique to the fruit axis. The base is somewhat shorter on the dorsal suture side of the fruit.

Apex:

*Form.*—Rounded in the area over the shoulders and depressed. The pistol point is apical, and in some fruit a stylar type opening is evident at the pistil point. This particular characteristic is especially noteworthy on fully matured fruit.

Stem:

*Generally.*—Short. A bulbous shaped area can be observed at the base of the stem. The length dimension of this bulbous shaped area is approximately 3–4.5 mm., and the thickness dimension is approximately 5 mm.

*Stem length.*—Approximately 4–6 mm.

*Stem thickness.*—Approximately 3 mm.

*Stem color.*—Green, (17-J-7).

Skin:

*Thickness.*—Average.

*Flavor.*—Mild.

*Tendency to crack.*—Not observed.

*Pubescence.*—Present, however it is very light.

*Color.*—A light orange color is evident at full commercial maturity, (10-K-8). The skin color is uniform, and no dots or speckling are generally evident. The fruit has a very clean appearance.

Flesh:

*Color.*—At full commercial maturity the flesh is a uniform orange, (10-G-11).

*Color — pit cavity.*—The pit cavity color is slightly darker and a moderate number of light yellow fibers are present.

*Texture.*—Generally — firm and crisp at commercial maturity. The variety becomes juicier with senescence.

*Flesh fibers — numbers.*—Average.

*Flesh fibers — length.*—Medium.

*Flesh fibers — color.*—Yellow.

*Flesh fibers — texture.*—Fine and tender.

*Ripening.*—Even.

*Flavor.*—Slightly acidic, however, it is considered rich and well above average for such an early maturing fresh market apricot.

*Aroma.*—Moderate and pleasant.

*Eating quality.*—Very good.

Stone:

*Generally.*—Freestone. Some slight attachment to the fruit may be evident along the ventral surface, however, the stone breaks away cleanly.

Size:

*Generally.*—average.

*Average length.*—Approximately 32 mm.

*Average width.*—Approximately 26 mm.

*Average thickness.*—Approximately 16 mm.

*Fibers.*—Generally — a few fibers appear along the ventral suture.

*Form.*—Generally — very roughly oval.

*Base.*—Form — rounded and may appear very slightly truncate. The base angle appears obliquely oriented with respect to the stone axis.

*Hilum — Generally.*—Small and moderately eroded.

*Hilum — Shape.*—Roughly oval.

*Apex.*—Shape — rounded, and having no point evident. The apex is positioned in an oblique plane with respect to the stone axis.

*Sides.*—Generally equal, although some variability may be noted from time to time.

*Stone surface.*—Texture — moderately rough. One groove appearing in the stone surface is positioned in an attitude roughly parallel to the ventral suture and further is located approximately 4–6 mm. below same. Several irregular pits generally appear in the stone surface and are usually located laterally and just below the apex.

*Ventral edge.*—Shape — a thin prominent wing extends from the base to the apex.

*Dorsal edge.*—Generally — a deep groove is evident, and extends from the base to mid-suture. This same groove is generally not visible beyond the mid-suture line. The shape of the apical shoulder area of the suture is rounded and numerous small pits are evident. The dorsal edge is distinctive.

*Stone color.*—Dry — light brown, (12-G-7).

*Tendency to split.*—Not observed.

Fruit use: The subject variety "Judy's Delight" is a fresh market apricot for both local and long distance markets.

Storage quality: Good.

Shipping quality: The variety has not been shipped in volume, however, the firm crisp texture of the flesh at commercial maturity strongly indicates that this variety will have noteworthy shipping characteristics.

Although the new variety of apricot tree possesses the described characteristics as a result of the growing conditions prevailing in Fresno County, Calif., in the Central part of the San Joaquin Valley, it is to be understood that variations of the usual magnitude and characteristics incident to growing conditions, fertilization, pruning and pest control are to be expected.

Having thus described and illustrated our new variety of apricot tree, what is claimed as new and desired to be secured by Letters Patent is:

1. A new and distinct variety of apricot tree substantially as illustrated and described and which is somewhat similar to the Katy Apricot Tree (U.S. Plant Pat. No. 4,339) with which it is most closely related in its date of harvesting but from which it is distinguished therefrom and characterized principally as to novelty by bearing fruit which are larger in size and have a uniform skin color which is a lighter shade of orange than that characteristically displayed by the fruit produced by the Katy Apricot Tree, the fruit of the subject variety ripening for commercial harvesting and shipment approximately May 15 through May 30 in the San Joaquin Valley of central California.

* * * * *

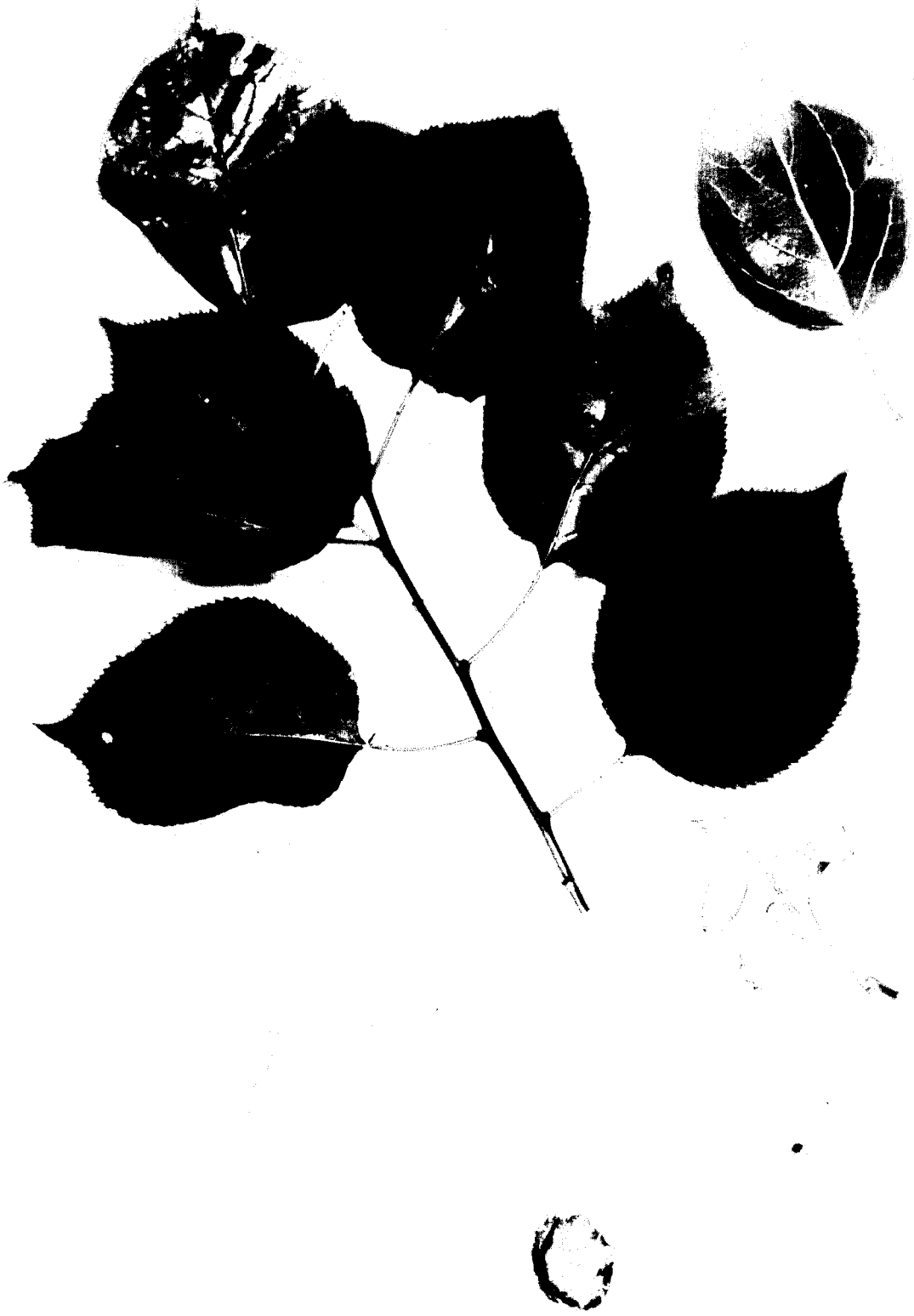

UNITED STATES PATENT AND TRADEMARK OFFICE

CERTIFICATE OF CORRECTION

PATENT NO. : PP 6,923

DATED : July 18, 1989

INVENTOR(S) : Hurado et al.

It is certified that error appears in the above-identified patent and that said Letters Patent is hereby corrected as shown below:

Column 4, Line 22, delete "lower" and substitute ---flower---.

Column 4, Line 54, delete "cvity" and substitute ---cavity---.

Column 4, Line 57, delete "somehwat" and substitute ---somewhat---.

Column 5, Line 2, delete "pistol" and substitute ---pistil---.

Column 6, Line 58, capitalize the word "Central".

Signed and Sealed this

Fifteenth Day of May, 1990

*Attest:*

HARRY F. MANBECK, JR.

*Attesting Officer*

*Commissioner of Patents and Trademarks*